United States Patent [19]

Pak

[11] Patent Number: 5,703,127

[45] Date of Patent: Dec. 30, 1997

[54] COMPOSITION, DOSAGE UNIT, AND METHOD FOR TREATING STOMACH DISORDERS

[76] Inventor: Kyoungsik Pak, 371 Sweetbriar Rd., King of Prussia, Pa. 19406

[21] Appl. No.: 591,889

[22] Filed: Jan. 25, 1996

[51] Int. Cl.$^6$ .................. A61K 31/205; A61K 31/195
[52] U.S. Cl. .................. 514/562; 514/556; 514/473; 514/53
[58] Field of Search .................. 514/556, 562, 514/473, 53

[56] References Cited

FOREIGN PATENT DOCUMENTS 9533486  12/1995  WIPO .

OTHER PUBLICATIONS

DiPiro et al. "Pharmacotherapy A Pathophysiologic Approach" Elsevier Science, New York, 1989, p. 20.
HCAPLUS Abstract 1970: 41562 Gasparini (1969).
HCAPLUS Abstract 1996: 147790 Riga, D. et al. (1995).
*National Formulary XIII*, published by the American Pharmaceutical Association, pp. 434–437 (Sep. 1, 1970).
*Physician's Desk Reference*, published by Medical Economies, Inc., p. 533 (1966).
*Physician's Desk Reference*, published by Medical Economies, Inc., p. 526 (1966).
*The United States Pharmacopeia*, published by United States Pharmacopeia Convention, Inc., pp. 342–343 (1980).
*The United States Pharmacopeia*, published by the United States Pharmacopeia Convention, Inc., p. 506 (1980).
*National Formulary XIII*, published by the American Pharmeutiacl Association, pp. 320–321 (1970).
*The Merck Index Eleventh Edition*, p. 1581 (1989).
USPXX (re: Fructose), one page (Jul. 1, 1980).
USPXX (re: Methionine), one page (Jul. 1, 1980).
*Merck Index Ninth Edition*, one page (re: Methionine) (1976).

*Modern Nutrition in Health and Disease*, edited by Maurice E. Shils & Vernon R. Young, pp. 1363–1365 (1986).
*Modern Nutrition in Health and Disease*, edited by Maurice E. Shil & Vernon R. Young, p. 44 (1986).
*Gastrointestinal Health*, by Steven P. Peikin, pp. 44–45 (1991).
*Physician's Gen RX—The Complete Drug Reference*, p. II–1276 (1995).
*Nutrition Desk Reference*, by Robert H. Garrison, Jr., M.A.R. Ph., & Elizabeth Somer, M.A., pp. 13 and 22–23 (1985).
*Physician's Desk Reference*, Reid Laboratories Inc., p. 770 (1962).
*The Doctors' Vitamin and Mineral Encyclopedia*, by Sheldon Saul Handler, M.D., Ph.D pp. 224–225 (1990).
"Sulphydryl–Containing Agents Stimulate the Health of Duodenal Ulceration in Man" by Aws S. Salim, *Pharmacology* 1992;45:170–180.
"Gastric Mucosal Cytoprotection in the Rat by Cysteine" by Aws S. Salim, *J. Pharm. Pharmacol.* 1987, 39:553–555.
"Incorporation of 35S L–Methionine by the Rat With Steroid Ulceration" by Turner et al., *The Journal of Maine Medical Association*, vol. 68 pp. 227–231, Jul. 1977.
"Sulphydryl–Containing Agents & the Prevention of Duodenal Ulcer Relapse" by Aws S. Salim, *Pharmacology* 1993; 46:281–288.
"Sulphydryl–Containing Agents: A New Approach to the Problem of Refractory Peptic Ulceration" by Aws S. Salim, *Pharmacology* 1992;45:301–306.

*Primary Examiner*—Marianne M. Cintins
*Assistant Examiner*—M. Moezie
*Attorney, Agent, or Firm*—John F. A. Earley; John F. A. Earley, III

[57] ABSTRACT

A dosage unit for treating stomach disorders, comprises an effective dosage of L- or DL-Methionine, and an effective dosage of a sweetener.

15 Claims, No Drawings

COMPOSITION, DOSAGE UNIT, AND METHOD FOR TREATING STOMACH DISORDERS

BACKGROUND OF THE INVENTION

1. Field of the Invention

This invention relates to the field of treating stomach disorders, such as heartburn, stomach pain, gastritis, peptic ulcers, hyperacidity, and the like, and is specifically concerned with a composition for treating such stomach disorders, a dosage unit for treating such stomach disorders, and a method of treating such stomach disorders.

2. Description of the Prior Art

Methionine is a sulfur containing essential amino acid. In human beings, Methionine acts to repair damaged cells of skin, nails, and hair, helps prevent disorders of mucous membranes, and helps prevent disorders of the nervous system. Methionine also helps regulate body metabolism.

Carbohydrates supply energy to the human body and help the human body to build cells.

SUMMARY OF THE INVENTION

It is an object of the invention to provide a composition, a dosage unit thereof, and a method for treating stomach disorders.

Further, it is an object of the invention to provide a composition, a dosage unit thereof, and a method for treating stomach disorders which helps to relieve heartburn and stomach pain quickly, aids healing of gastritis and peptic ulcers, and controls hyperacidity.

It is another object of the invention to provide a composition, a dosage unit thereof, and a method for treating stomach disorders, which is based on L- or DL-Methionine, which eliminates the disadvantage of the unpleasant taste of the Methionine, and which supplies energy to the patient which assists the digestion of food.

These and other objects of the invention are accomplished by my invention, which is described below.

DETAILED DESCRIPTION OF THE INVENTION

In accordance with the invention, a composition for treating stomach disorders, such as heartburn, stomach pain, gastritis, peptic ulcers, hyperacidity, and the like, comprises L- or DL-Methionine and a sweetener.

The invention also includes a dosage unit for treating stomach disorders, such as heartburn, stomach pain, gastritis, peptic ulcers, hyperacidity, and the like, which comprises an effective dosage of L- or DL-Methionine and an effective dosage of a sweetener.

Further, the invention includes a method of treating stomach disorders, such as heartburn, stomach pain, gastritis, peptic ulcers, hyperacidity, and the like, which comprises the steps of providing an effective dosage of L- or DL-Methionine, ingesting the effective dosage of L-or DL-Methionine to place the L- or DL-Methionine in the stomach of a patient having a stomach disorder to be treated, and treating the stomach disorder with the L- or DL-Methionine to provide relief from discomfort caused by the disorder. Preferably, the L- or DL-Methionine is ingested 30 minutes after the patient has eaten a meal. Preferably, the L- or DL-Methionine is first mixed into an effective amount of water to form a mixture, and the patient drinks the mixture to place the mixture in the patient's stomach. The water aids in dispersing the Methionine throughout the treatment area (e.g., the patient's stomach, esophagus, and intestine) to provide relief throughout the treatment area and to control the disorder. Further, Methionine in this aqueous mixture form is easier to digest. Also, preferably, a sweetener is mixed into the mixture.

The L- or DL-Methionine, in an effective amount, provides relief of heartburn and stomach pain quickly, aids healing of gastritis and peptic ulcers, and controls hyperacidity. Further, the L- or DL-Methionine, in an effective dosage, ingested in accordance with the invention, stops minor diarrhea. DL-Methionine is preferred.

The sweetener eliminates the unpleasant taste of Methionine. Further, the sweetener supplies energy to a patient, which results in aiding digestion of food by the patient. The sweetener may be fructose, dextrose, or sucrose, for example, and preferably is fructose, which is sweeter than sucrose and which may be eaten by diabetics.

The ranges for each component of the composition preferably are about 25% to about 50% L- or DL-Methionine by weight of the composition, and about 50% to about 75% sweetener by weight of the composition. However, the amount of each component may extend outside these ranges. A composition comprising about 33% L- or DL-Methionine by weight of the composition and about 67% sweetener by weight of the composition is most preferred.

Preferably, the dosage of L- or DL-Methionine is about 1 gram. Also, preferably, the dosage of sweetener is in a range of about 1 gram to about 3 grams, and more preferably is in a range of about 1 gram to about 2 grams. A dosage unit comprising 1 gram of L- or DL-Methionine and 1.5 grams of sweetener is most preferred.

I now turn to the examples of the invention, all ingredients being by weight unless indicated otherwise.

EXAMPLE 1

Patients suffering from the discomfort of stomach disorders such as heartburn, stomach pain, gastritis, peptic ulcers, hyperacidity, and the like are treated for this discomfort by drinking an aqueous mixture comprising 1 gram of DL-Methionine that has been stirred into 2 ounces of water. For the patients who drank the aqueous mixture on a full stomach (e.g., 30 minutes after finishing a meal), relief was obtained typically within 20 to 30 minutes, and in very bad stomach disorder cases within 2–3 hours.

In cases where the aqueous mixture was taken on an empty stomach, it took longer (typically 3 hours) for relief from the discomfort caused by the stomach disorder to occur. Further, in these cases, many patients incurred side effects such as indigestion, weakness, and unpleasant feeling, until the relief occurred. Accordingly, preferably it is desired to ingest the Methionine on a full stomach.

EXAMPLE 2

The ingredients of the following formulation are stirred well into 2 ounces of water to form an aqueous mixture, and the aqueous mixture is drunk by a patient suffering from a stomach disorder such as heartburn, stomach pain, gastritis, peptic ulcers, hyperacidity, and the like:

| Component | Percentage | Grams |
|---|---|---|
| DL-Methionine | 40.0 | 1.0 |
| Fructose | 60.0 | 1.5 |
| | 100.0 | 2.5 |

Within about 30 minutes, relief from the discomfort caused by the stomach disorder was felt by the patient.

The procedure set out in this example was repeated with a number of patients suffering from stomach disorders, and the most effective relief to discomfort caused by the stomach disorders was obtained by drinking the aqueous mixture three times a day, preferably after each meal.

Also, I found that the best results were obtained when the aqueous mixture was not taken on an empty stomach. However, relief from the discomfort caused by a stomach disorder was obtained even when the aqueous mixture was taken on an empty stomach.

With the inclusion of a sweetener, the side effects such as those associated with taking Methionine in accordance with Example 1 on an empty stomach occurred less frequently and with less severity. The patients reported that the unpleasant taste of the Methionine was eliminated.

The following examples 3–26 further illustrate the invention. The ingredients of the formulations in these examples are all by weight, and the procedures set out in Example 2 are used with the formulations set out in these examples, resulting in results similar those obtained in Example 2. With the inclusion of a sweetener, the side effects such as those associated with taking Methionine in accordance with Example 1 on an empty stomach occurred less frequently and with less severity. Also, in examples 3–25, the patients reported that the unpleasant taste of the Methionine was eliminated.

EXAMPLE 3

| Component | Percentage | Grams |
|---|---|---|
| DL-Methionine | 33.3 | 1.0 |
| Fructose | 66.7 | 2.0 |
| | 100.0 | 3.0 |

EXAMPLE 4

| Component | Percentage | Grams |
|---|---|---|
| DL-Methionine | 50.0 | 1.0 |
| Fructose | 50.0 | 1.0 |
| | 100.0 | 2.0 |

EXAMPLE 5

| Component | Percentage | Grams |
|---|---|---|
| DL-Methionine | 25.0 | 1.0 |
| Fructose | 75.0 | 3.0 |
| | 100.0 | 4.0 |

EXAMPLE 6

| Component | Percentage | Grams |
|---|---|---|
| DL-Methionine | 40.0 | 1.0 |
| Fructose | 60.0 | 1.5 |
| | 100.0 | 2.5 |

EXAMPLE 7

| Component | Percentage | Grams |
|---|---|---|
| DL-Methionine | 33.3 | 1.0 |
| Fructose | 66.7 | 2.0 |
| | 100.0 | 3.0 |

EXAMPLE 8

| Component | Percentage | Grams |
|---|---|---|
| DL-Methionine | 50.0 | 1.0 |
| Fructose | 50.0 | 1.0 |
| | 100.0 | 2.0 |

EXAMPLE 9

| Component | Percentage | Grams |
|---|---|---|
| DL-Methionine | 25.0 | 1.0 |
| Fructose | 75.0 | 3.0 |
| | 100.0 | 4.0 |

EXAMPLE 10

| Component | Percentage | Grams |
|---|---|---|
| DL-Methionine | 40.0 | 1.0 |
| Dextrose | 60.0 | 1.5 |
| | 100.0 | 2.5 |

EXAMPLE 11

| Component | Percentage | Grams |
|---|---|---|
| DL-Methionine | 33.3 | 1.0 |
| Dextrose | 66.7 | 2.0 |
| | 100.0 | 3.0 |

EXAMPLE 12

| Component | Percentage | Grams |
|---|---|---|
| DL-Methionine | 50.0 | 1.0 |

-continued

| Component | Percentage | Grams |
|---|---|---|
| Dextrose | 50.0 | 1.0 |
|  | 100.0 | 2.0 |

EXAMPLE 13

| Component | Percentage | Grams |
|---|---|---|
| DL-Methionine | 25.0 | 1.0 |
| Dextrose | 75.0 | 3.0 |
|  | 100.0 | 4.0 |

EXAMPLE 14

| Component | Percentage | Grams |
|---|---|---|
| DL-Methionine | 40.0 | 1.0 |
| Sucrose | 60.0 | 1.5 |
|  | 100.0 | 2.5 |

EXAMPLE 15

| Component | Percentage | Grams |
|---|---|---|
| DL-Methionine | 33.3 | 1.0 |
| Sucrose | 66.7 | 2.0 |
|  | 100.0 | 3.0 |

EXAMPLE 16

| Component | Percentage | Grams |
|---|---|---|
| DL-Methionine | 50.0 | 1.0 |
| Sucrose | 50.0 | 1.0 |
|  | 100.0 | 2.0 |

EXAMPLE 17

| Component | Percentage | Grams |
|---|---|---|
| DL-Methionine | 25.0 | 1.0 |
| Sucrose | 75.0 | 3.0 |
|  | 100.0 | 4.0 |

EXAMPLE 18

| Component | Percentage | Grams |
|---|---|---|
| DL-Methionine | 40.0 | 1.0 |

-continued

| Component | Percentage | Grams |
|---|---|---|
| Dextrose | 60.0 | 1.5 |
|  | 100.0 | 2.5 |

EXAMPLE 19

| Component | Percentage | Grams |
|---|---|---|
| DL-Methionine | 33.3 | 1.0 |
| Dextrose | 66.7 | 2.0 |
|  | 100.0 | 3.0 |

EXAMPLE 20

| Component | Percentage | Grams |
|---|---|---|
| DL-Methionine | 50.0 | 1.0 |
| Dextrose | 50.0 | 1.0 |
|  | 100.0 | 2.0 |

EXAMPLE 21

| Component | Percentage | Grams |
|---|---|---|
| DL-Methionine | 25.0 | 1.0 |
| Dextrose | 75.0 | 3.0 |
|  | 100.0 | 4.0 |

EXAMPLE 22

| Component | Percentage | Grams |
|---|---|---|
| DL-Methionine | 40.0 | 1.0 |
| Sucrose | 60.0 | 1.5 |
|  | 100.0 | 2.5 |

EXAMPLE 23

| Component | Percentage | Grams |
|---|---|---|
| DL-Methionine | 40.0 | 1.0 |
| Sucrose | 66.7 | 2.0 |
|  | 100.0 | 3.0 |

EXAMPLE 24

| Component | Percentage | Grams |
|---|---|---|
| DL-Methionine | 50.0 | 1.0 |

| Component | Percentage | Grams |
|---|---|---|
| Sucrose | 50.0 | 1.0 |
|  | 100.0 | 2.0 |

EXAMPLE 25

| Component | Percentage | Grams |
|---|---|---|
| DL-Methionine | 25.0 | 1.0 |
| Sucrose | 75.0 | 3.0 |
|  | 100.0 | 4.0 |

EXAMPLE 26

| Component | Percentage | Grams |
|---|---|---|
| DL-Methionine | 66.7 | 1.0 |
| Fructose | 33.3 | 0.5 |
|  | 10.0 | 1.5 |

EXAMPLE 27

The ingredients of the following formulation were stirred into 1 cc of water to form an aqueous mixture for treating stomach disorders. Such an aqueous mixture relieved discomfort from stomach ailments when drank by a majority of patients. However, in some patients relief was not obtained, and in these cases, I believe this may be due to irritation of wounds of the mucous membranes of the digestive track of these patients from the honey.

| Component | Percentage | Grams |
|---|---|---|
| DL-Methionine | 16.7 | 1.0 |
| Alfalfa Honey | 83.3 | 5.0 |
|  | 100.0 | 6.0 |

The ingredients for each formulation of the invention may be mixed together to form the composition and the dosage unit of the invention. Preferably, each dosage unit is packaged individually, and may be mixed into water when treatment is needed.

Optionally, the individual ingredients of each formulation of the invention may be mixed individually into water to form an aqueous mixture when treatment is needed.

ADVANTAGES

1) The inventive composition and the inventive dosage unit is made of only nutrients, Methionine and sweetener, which are needed by the human body. These ingredients are very safe and beneficial to the human body, and Methionine is approved by the U.S. Food and Drug Administration (FDA Pre 1938 Drugs).

Methionine is a sulfur containing essential amino acid. In human beings, Methionine acts to repair damaged cells of skin, nails, and hair, helps prevent disorders of mucous membranes, and helps prevent disorders of the nervous system. Methionine also helps regulate body metabolism.

The sweeteners are carbohydrates. For example, fructose, a monosaccharide, supplies energy.

Accordingly, in addition to providing relief from the discomfort of stomach disorders, the patient receives nutrients when treating stomach disorders in accordance with the invention.

2) I believe that the Methionine may act as an antibacterial agent, which may kill H. pylori bacteria which causes peptic ulcers, and as a local anesthetic, providing a pain relieving effect in the digestive tract.

3) Because the inventive composition and dosage unit thereof comprise only of nutrients, there are very few side effects, if any, when taken to treat stomach disorders.

4) Treatment of stomach disorders in accordance with the invention provides quick and effective relief to the discomforts caused by stomach disorders. discomforts caused by stomach disorders.

I claim:

1. A composition for treating discomfort caused by heartburn, stomach pain, gastritis, reflux, or hyperacidity, consisting essentially of L- or DL-Methionine, and means for sweetening and for reducing the frequency and severity of undesirable side effects of the L- or DL-Methionine, wherein said means is a sweetener, wherein the L- or DL-Methionine is present in a range of about 25% to about 50% by weight of the composition, wherein the sweetener is present in a range of about 50% to about 75% by weight of the composition, and wherein the sweetener is fructose, dextrose, or sucrose.

2. The composition of claim 1, wherein the L- or DL-Methionine is present in an amount of about 33% by weight of the composition, and the sweetener is present in an amount of about 67% by weight of the composition.

3. The composition of claim 1, wherein the L- or DL-Methionine is present in an amount of about 33% by weight of the composition, and the sweetener is present in an amount of about 67% by weight of the composition, and the sweetener is fructose.

4. The composition of claim 1, wherein the L- or DL-Methionine is present in an amount of about 40% by weight of the composition, the sweetener is present in an amount of about 60% by weight of the composition, and the sweetener is fructose.

5. A dosage unit for treating discomfort caused by heartburn, stomach pain, gastritis, reflux, or hyperacidity, consisting essentially of an effective dosage of L- or DL-Methionine, and an effective dosage of means for sweetening and for reducing the frequency and severity of undesirable side effects of the L- or DL-Methionine, wherein said means is a sweetener, wherein the L- or DL-Methionine is present in a range of about 25% to about 50% by weight of the composition, wherein the sweetener is present in a range of about 50% to about 75% by weight of the composition, and wherein the sweetener is fructose, dextrose, or sucrose.

6. The dosage unit of claim 5, wherein the L- or DL-Methionine is present in an amount of about 33% by weight of the dosage unit, and the sweetener is present in an amount of about 67% by weight of the dosage unit.

7. The dosage unit of claim 5, wherein the L- or DL-Methionine is present in an amount of about 33% by weight of the dosage unit, the sweetener is present in an amount of about 67% by weight of the dosage unit, and the sweetener is fructose.

8. The dosage unit of claim 5, wherein the dosage of L- or DL-Methionine is present in an amount of about 1 gram, and the dosage of the sweetener is present in a range of about 1 gram to about 3 grams.

9. The dosage unit of claim 5, wherein the dosage of L- or DL-Methionine is present in an amount of about 1 gram, and the dosage of the sweetener is present in a range of about 1 gram to about 2 grams.

10. The dosage unit of claim 8, wherein the dosage of sweetener is 1.5 grams.

11. A method of treating discomfort caused by heartburn, stomach pain, gastritis, reflux, or hyperacidity, consisting essentially of the steps of providing an effective dosage of L- or DL-Methionine and an effective dosage of means for sweetening and for reducing the frequency and severity of undesirable side effects of L- or DL-Methionine, orally ingesting the effective amount of L- or DL-Methionine and the effective amount of means for sweetening and for reducing the frequency and severity of undesirable side effects of the L- or DL-Methionine to place the L- or DL-Methionine and the means for sweetening and reducing the frequency of undesirable side effects of the L- or DL-Methionine in the stomach, and treating the discomfort with the L- or DL-Methionine to provide relief, wherein said means is a sweetener, wherein the sweetener is fructose, dextrose, or sucrose, wherein the dosage of L- or DL-Methionine is about 1 gram, and wherein the dosage of the sweetener is in a range of about 1 gram to about 3 grams.

12. The method of claim 11, wherein the L- or DL-Methionine is mixed into an effective amount of water to form a mixture before ingesting the L- or DL-Methionine.

13. The method of claim 11, wherein a sufficient amount of food is ingested to ensure that the stomach is not empty before ingesting the L- or DL-Methionine.

14. The method of claim 11, wherein the L- or DL-Methionine and sweetener are mixed into an effective amount of water to form a mixture before ingesting the L- or DL-Methionine and sweetener, and wherein the amount of water is about 2 ounces.

15. The method of claim 14, wherein the dosage of sweetener is 1.5 grams.

* * * * *